(12) United States Patent
Shin et al.

(10) Patent No.: US 11,339,421 B2
(45) Date of Patent: May 24, 2022

(54) LEUKEMIA DIAGNOSTIC KIT TARGETING PROHIBITIN GENE AND DIAGNOSTIC METHOD USING SAME

(71) Applicant: INDUSTRY FOUNDATION OF CHONNAM NATIONAL UNIVERSITY, Gwangju (KR)

(72) Inventors: Myung Guen Shin, Gwangju (KR); Hye Ran Kim, Gwangju (KR); Yong Gwan Won, Gwangju (KR)

(73) Assignee: INDUSTRY FOUNDATION OF CHONNAM NATIONAL UNIVERSITY, Gwangju (KR)

( * ) Notice: Subject to any disclaimer, the term of this patent is extended or adjusted under 35 U.S.C. 154(b) by 721 days.

(21) Appl. No.: 16/079,432

(22) PCT Filed: Feb. 21, 2017

(86) PCT No.: PCT/KR2017/001867
§ 371 (c)(1),
(2) Date: Aug. 23, 2018

(87) PCT Pub. No.: WO2017/146432
PCT Pub. Date: Aug. 31, 2017

(65) Prior Publication Data
US 2019/0048396 A1 Feb. 14, 2019

(30) Foreign Application Priority Data
Feb. 23, 2016 (KR) .......................... 10-2016-0021320

(51) Int. Cl.
*C12Q 1/68* (2018.01)
*C12Q 1/6806* (2018.01)
*C12Q 1/686* (2018.01)

(52) U.S. Cl.
CPC ............. *C12Q 1/6806* (2013.01); *C12Q 1/68* (2013.01); *C12Q 1/686* (2013.01); *C12Q 2600/112* (2013.01); *C12Q 2600/118* (2013.01); *C12Q 2600/158* (2013.01); *C12Q 2600/16* (2013.01); *C12Q 2600/166* (2013.01)

(58) Field of Classification Search
None
See application file for complete search history.

(56) References Cited

FOREIGN PATENT DOCUMENTS

| CA | 2483284 A1 | 5/2006 |
|----|------------|--------|
| EP | 0329822 A2 | 8/1989 |
| EP | 0439182 A2 | 7/1991 |
| KR | 10-2014-0056472 A | 5/2014 |
| WO | WO 88/10315 A1 | 12/1988 |
| WO | WO 89/06700 A1 | 7/1989 |
| WO | WO 90/01069 A1 | 2/1990 |
| WO | WO 90/06995 A1 | 6/1990 |

OTHER PUBLICATIONS

Kim, Hye-Ran et al. Diagnostic and prognostic implications of prohibitin over expression in normal karyotype acute myeloid leukemia. Blood, vol. 128(22), p. 1714, Dec. 2, 2016.*
European Search Report for EP17756770.8 dated Jun. 13, 2019 from European patent office in a counterpart European patent application.
Hajime Yurugi et al., "Expression of prohibitins on the surface of activated T cells", Biochemical and Biophysical Research Communications, vol. 420, pp. 275-280, 2012.
Kaisa J. Teittinen et al., "Nucleolar proteins with altered expression in leukemic cell lines", Leukemia Research, vol. 36, pp. 232-236, 2012.
European Communication Pursuant to Article 94(3) EPC for EP17756770.8 dated Nov. 11, 2020 from European patent office in a counterpart European patent application.
Nikolaos Soulitzis et al. "Downregulation of lung mitochondrial prohibitin in COPD", Respiratory Medicine, vol. 106, No. 7, 2012 (Mar. 23, 2012), pp. 954-961, XP028423481.
International Search Report for PCT/KR2017/001867 dated May 15, 2017.
Peng et al., "Multifaceted role of prohibitin in cell survival and apoptosis", Apoptosis, vol. 20, pp. 1135-1149, 2015.
Thuaud et al., "Prohibitin Ligands in Cell Death and Survival: Mode of Action and Therapeutic Potential", Chemistry & Biology, vol. 20, pp. 316-331, 2013.
Moncunill-Massaguer et al, "A novel prohibitin-binding compound induces the mitochondrial apoptotic pathway through NOXA and BIM upregulation", Oncotarget, vol. 6, No. 39, pp. 41750-41765, 2015.
He at al., "Prohibitin promotes apoptosis of promyelocytic leukemia induced by arsenic sulfide", International Journal of Oncology, vol. 47, pp. 2286-2295, 2015.

* cited by examiner

*Primary Examiner* — Suryaprabha Chunduru
(74) *Attorney, Agent, or Firm* — The PL Law Group, PLLC (57) ABSTRACT

A leukemia diagnostic kit may be an RT-PCR kit enabling expression levels of prohibitin-1 and prohibitin-2 to be checked in a leukemia patient specimen, wherein the accuracy and the reproducibility of leukemia diagnosis of the kit are higher than those of a conventional RT-PCR kit, thereby being useful as a kit for diagnosing leukemia, examining residual lesions and evaluating therapeutic effects.

4 Claims, 10 Drawing Sheets
Specification includes a Sequence Listing.

SEQUENCE LISTING

```
<160> NUMBER OF SEQ ID NOS: 4

<210> SEQ ID NO 1
<211> LENGTH: 19
<212> TYPE: DNA
<213> ORGANISM: Artificial Sequence
<220> FEATURE:
<223> OTHER INFORMATION: PRIMER

<400> SEQUENCE: 1
ggaggcgtgg tgaactctg                                              19

<210> SEQ ID NO 2
<211> LENGTH: 20
<212> TYPE: DNA
<213> ORGANISM: Artificial Sequence
<220> FEATURE:
<223> OTHER INFORMATION: PRIMER

<400> SEQUENCE: 2
ctggcacatt acgtggtcga                                             20

<210> SEQ ID NO 3
<211> LENGTH: 20
<212> TYPE: DNA
<213> ORGANISM: Artificial Sequence
<220> FEATURE:
<223> OTHER INFORMATION: PRIMER

<400> SEQUENCE: 3
cttggttcca gtaccccatt                                             20

<210> SEQ ID NO 4
<211> LENGTH: 19
<212> TYPE: DNA
<213> ORGANISM: Artificial Sequence
<220> FEATURE:
<223> OTHER INFORMATION: PRIMER

<400> SEQUENCE: 4
cgagacaaca ctcgcaggg                                              19
```

LEUKEMIA DIAGNOSTIC KIT TARGETING PROHIBITIN GENE AND DIAGNOSTIC METHOD USING SAME

CROSS REFERENCE TO RELATED APPLICATIONS AND CLAIM OF PRIORITY

This application claims benefit under 35 U.S.C. 119(e), 120, 121, or 365(c), and is a National Stage entry from International Application No. PCT/KR2017/001867, filed Feb. 21, 2017, which claims priority to the benefit of Korean Patent Application No. 10-2016-0021320 filed on Feb. 23, 2016 in the Korean Intellectual Property Office, the entire contents of which are incorporated herein by reference

TECHNICAL FIELD

The present invention relates to a leukemia diagnostic kit and a diagnostic method using the same.

BACKGROUND ART

While various causes of leukemia among blood cancers have been known, it has been most generally known that leukemia results from gene mutations and chromosomal mutations including the same. Prognosis may vary depending on the type of chromosomal mutation, and a therapeutic regimen for a leukemia patient may be determined thereby.

Currently, leukemia is diagnosed using cytomorphological findings, immunophenotyping findings, and chromosomal mutations including gene mutations. To detect gene and chromosomal mutations, molecular genetic methods based on traditional chromosome testing and polymerase chain reaction (PCR) have been used, and various studies have been conducted to develop various molecular genetic testing methods which can be easily applied in actual investigation sites.

For example, a diagnostic method combined with a method of identifying the arrangement of a fusion gene using long distance inverse polymerase chain reaction, and a method using PCR or reverse transcription (RT)-PCR performed on DNA of somatic cells have been developed.

However, among the above-mentioned methods, FISH, which a method of directly detecting individual cells with a chromosomal translocation, cannot detect cells at the early stage of leukemia, and a method using PCR or RT-PCR has high sensitivity, but a false-positive reaction may occur due to the contamination of a specimen, and it is difficult to exactly determine the progression of the disease.

To overcome the above-mentioned disadvantages, recently, leukemia diagnostic kits utilizing a real-time PCR method which can also quantify target RNA from a small amount of a specimen have been developed and purchased, but even for a specimen obtained from one patient, various genes involved in the development of leukemia have to be investigated to improve the accuracy of diagnosis, and therefore there is a disadvantage in that it is difficult to more rapidly diagnose leukemia due to considerable costs and time.

SUMMARY

It is an object of the present invention to provide a kit for diagnosing leukemia by combining an expression level of a prohibitin-1 (PHB1) gene and an expression level of a prohibitin-2 (PHB2) gene to solve a conventional problem of examining various genes involved in the development of leukemia to improve the accuracy of diagnosis, and perform rapid diagnosis of leukemia, and a method of diagnosing leukemia.

1. A leukemia diagnostic kit, which includes a PHB1 gene including a forward primer of SEQ ID NO: 1 and a reverse primer of SEQ ID NO: 2; and a PHB2 gene including a forward primer of SEQ ID NO: 3 and a reverse primer of SEQ ID NO: 4.

2. The leukemia diagnostic kit described above in 1, which is for measuring and comparing an expression level of the PHB1 gene and an expression level of the PHB2 gene.

3. The leukemia diagnostic kit described above in 1, wherein the diagnosis of leukemia is determined by any one equation selected from the group consisting of Equations 1 to 3:

$$Y=T-x_2 \quad \text{[Equation 1]}$$

(In Equation 1,
T is a boundary value between expression values of PHB2 in a normal group and a patient group,
$x_2$ is an expression value of PHB2,
when Y is a positive value, it is determined as "normal," and when Y is a negative value, it is determined as "patient.")

$$Y=0.5857x_1-4.7252x_2-0.18652 \quad \text{[Equation 2]}$$

(In Equation 2,
$x_1$ is an expression value of PHB1,
$x_2$ is an expression value of PHB2,
when Y is a positive value, it is determined as "normal," and when Y is a negative value, it is determined as "patient.")

$$Y=0.99 \times g(-4.536x_1+12.3963x_2+5.7187)-9.5315 \times g(51.402x_1-3.3215x_2+49.6252)+9.0499 \quad \text{[Equation 3]}$$

(In Equation 3,
g is a function defined by Equation 4,
when Y is a positive value, it is determined as "normal," and when Y is a negative value, it is determined as "patient.")

$$g(m) = \frac{1}{1+e^{-m}} \quad \text{[Equation 4]}$$

4. The leukemia diagnostic kit described above in 1, which is used to perform RT-PCR with respect to mRNA of the PHB1 gene and the PHB2 gene.

5. The leukemia diagnostic kit described above in 1, further including a reagent for PCR.

6. The leukemia diagnostic kit described above in 1, further including a reagent for RNA extraction.

7. The leukemia diagnostic kit described above in 1, wherein the leukemia is acute myelogenous leukemia, acute lymphocytic leukemia, chronic myelogenous leukemia or chronic lymphocytic leukemia.

8. A method of diagnosing leukemia using the leukemia diagnostic kit described in 1, which includes diagnosing leukemia by measuring expression levels of a prohibitin-1 (PHB1) gene and a prohibitin-2 (PHB2) gene and comparing the gene expression levels.

9. The method according to 8, wherein the diagnosis of leukemia is determined by any one equation selected from the group consisting of Equations 1 to 3:

$$Y=T-x_2 \quad \text{[Equation 1]}$$

(In Equation 1,
T is a boundary value between expression values of PHB2 in a normal group and a patient group,
$x_2$ is an expression value of PHB2,
when Y is a positive value, it is determined as "normal," and when Y is a negative value, it is determined as "patient.")

$$Y=0.5857x_1-4.7252x_2-0.18652 \quad \text{[Equation 2]}$$

(In Equation 2,
$x_1$ is an expression value of PHB1,
$x_2$ is an expression value of PHB2,
when Y is a positive value, it is determined as "normal," and when Y is a negative value, it is determined as "patient.")

$$Y=0.99 \times g(-41.536x_1+12.3963x_2+5.7187)-9.5315 \times g(51.402x_1-3.3215x_2+49.6252)+9.0499 \quad \text{[Equation 3]}$$

(In Equation 3,
g is a function defined by Equation 4,
when Y is a positive value, it is determined as "normal," and when Y is a negative value, it is determined as "patient.")

$$g(m) = \frac{1}{1+e^{-m}} \quad \text{[Equation 4]}$$

A leukemia diagnostic kit according to the present invention is a kit for RT-PCR to confirm degrees of the expression of PHB1 and PHB2 in a specimen of a leukemia patient, and can be effectively used as a kit for diagnosing leukemia, measuring a residual lesion and determining a therapeutic effect due to higher accuracy and reproducibility of the diagnosis of leukemia than a conventional RT-PCR kit.

DETAILED DESCRIPTION

Hereinafter, various aspects and a variety of exemplary embodiments of the present invention will be described in further detail.

The present invention provides a leukemia diagnostic kit, which includes a PHB1 gene including a forward primer of SEQ ID NO: 1 and a reverse primer of SEQ ID NO: 2; and a PHB2 gene including a forward primer of SEQ ID NO: 3 and a reverse primer of SEQ ID NO: 4.

According to the present invention, the leukemia diagnostic kit may be effectively used in measurement of a residual lesion and determination of a therapeutic effect as well as diagnosis, and the leukemia in the present invention includes acute myelogenous leukemia, acute lymphocytic leukemia, chronic myelogenous leukemia or chronic lymphocytic leukemia.

The leukemia diagnostic kit of the present invention may be used to perform RT-PCR with respect to mRNA of a PHB1 gene and a PHB2 gene.

According to the present invention, to obtain mRNA, white blood cells are obtained from specimens, preferably, peripheral blood and bone marrow specimens, and then total RNA is isolated therefrom. The separation of total RNA may be performed according to a conventional method known in the art. For example, total RNA in the cells may be easily isolated using TRIZOL.

Subsequently, cDNA is synthesized using the isolated mRNA as a template, and the cDNA is amplified. Since the total RNA of the present invention is isolated from a human sample, a poly-A tail is present at the end of mRNA, and cDNA may be easily synthesized using an oligo dT primer and a reverse transcriptase which utilize such a sequence characteristic. Subsequently, the synthesized cDNA is amplified using real-time PCR.

The primer used in the present invention forms a double-stranded structure by hybridization or annealing at one region of the template. Suitable conditions for nucleic acid hybridization to form such a double-stranded structure are disclosed in Joseph Sambrook et al., Molecular Cloning, A Laboratory Manual, Cold Spring Harbor Laboratory Press, Cold Spring Harbor, N.Y. (2001) and Haymes, B. D. et al., Nucleic Acid Hybridization, A Practical Approach, IRL Press, Washington, D.C. (1985). In the present invention, annealing or hybridization is performed under strict conditions which allow specific binding between a target nucleotide sequence and a primer. The strict conditions for annealing are sequence-dependent, and vary according to environmental variables.

Various DNA polymerases may be used in amplification of the present invention, and include the "Klenow" fragment of *E. coli* DNA polymerase I, a thermally stable DNA polymerase and bacteriophage T7 DNA polymerase. Preferably, the polymerases are thermally stable DNA polymerases obtained from a variety of bacterial species, and include *Thermus aquaticus* (Taq), *Thermus thermophilus* (Tth), *Thermus filiformis*, *Thermis flavus*, *Thermococcus literalis* and *Pyrococcus furiosus* (Pfu).

When polymerization is performed, excessive components required for a reaction are preferably provided to a reaction container. The excessive amount of the components required for an amplification reaction refers to the amount of a component such that the amplification reaction is not substantially limited by a concentration of the component. It is required that a cofactor such as Mg', dATP, dCTP, dGTP and dTTP are provided to a reaction mixture to an extent that the desired degree of amplification can be achieved.

All enzymes used in the amplification may be active under the same reaction conditions. In fact, a buffer solution allows all enzymes to approach the optimal reaction conditions. Therefore, the amplification of the present invention may be performed on a single reactant without a change in conditions such as the addition of a reactant.

The term "amplification" used herein refers to a reaction of amplifying a nucleic acid molecule. Various amplification reactions are reported in the art, and include, but are not limited to, PCR, RT-PCR, ligase chain reaction (LCR), Gap-LCR, repair chain reaction, transcription-mediated amplification (TMA), self-sustained sequence replication, selective amplification of target polynucleotide sequences, consensus sequence primed polymerase chain reaction (CP- PCR), arbitrarily primed polymerase chain reaction (AP-PCR), nucleic acid sequence based amplification (NASBA), strand displacement amplification and loop-mediated isothermal amplification (LAMP). Other amplification methods used herein are disclosed in U.S. Pat. Nos. 5,242,794, 5,494,810 and 4,988,617, and U.S. patent Ser. No. 09/854,317.

In the most exemplary embodiment of the present invention, amplification is performed according to PCR disclosed in U.S. Pat. Nos. 4,683,195, 4,683,202 and 4,800,159.

Meanwhile, PCR is the most well-known nucleic acid amplification method, and various modifications and applications are developed. For example, to improve the specificity or sensitivity of PCR, touchdown PCR, hot-start PCR, nested PCR and booster PCR were developed by modifying traditional PCR procedures. In addition, real-time PCR, differential display PCR (DD-PCR), rapid amplification of cDNA ends (RACE), multiplex PCR, inverse polymerase chain reaction (IPCR), vectorette PCR, thermal asymmetric interlaced PCR (TAIL-PCR) and multiplex PCR were developed for specific applications.

A primer used in the amplification reaction in the present invention is an oligonucleotide having a sequence complimentary to the cDNA sequence of PHB1 or PHB2. The term "primer" used herein refers to a single-stranded oligonucleotide which can act as the initiation point of template-directed DNA synthesis under suitable conditions (that is, four types of different nucleoside triphosphates and polymerases) in a suitable buffer solution at a suitable temperature. Suitable lengths of the primers may vary according to various factors, for example, a temperature and the use of a primer, and are typically 15-30 nucleotides. A short primer molecule generally requires a lower temperature to form a sufficiently stable hybrid complex with a template.

The primer sequence does not need a sequence perfectly complementary to a part of the sequence of the template, and it is enough to have sufficient complementarity within a range at which the primer is hybridized with the template to exhibit the specific function of the primer.

As an example, the primer used in the present invention has a sequence perfectly complementary to the cDNA sequence of PHB1 or PHB2. The primer of the present invention may be prepared using a sequence complementary to the mRNA (that is, cDNA) sequence of PHB1 disclosed in SEQ ID NO: 1, and may be prepared using a sequence complementary to the mRNA (that is, cDNA) sequence of PHB2 disclosed in SEQ ID NO: 3.

Such a primer may be designed by those of ordinary skill in the art with reference to the cDNA sequence of PHB1 or PHB2 using, for example, a program for designing a primer (e.g., PRIMER 3 program).

Degrees of the expression of PHB1 and PHB2 genes are investigated by analyzing cDNA of the amplified PHB1 or PHB2. For example, the expression level of PHB1 or PHB2 is measured by applying a mixture prepared by mixing cDNA, the primers synthesized using sequences complementary to PHB1 and PHB2 genes with an SYBR Green I reagent to RT-PCR. Here, to remove a difference in the expression of individual genes, the expression level of the β-actin gene widely known to be associated with a housekeeping gene may be simultaneously measured.

Through such an amplification reaction, measured values of the expression level of the PHB1 gene and the expression level of the PHB2 gene may be obtained with respect to a patient group and a normal group, as shown in FIGS. 1A to 1C and FIGS. 2A to 2C, through such real-time quantitative PCR.

The diagnosis of leukemia may be determined by any one equation selected from the group consisting of Equations 1 to 3 below, and the boundary values or boundary lines applied to Equations 1 to 3 in the present invention may be determined by mathematical, statistical, artificial intelligence and data-mining methods which are conventionally and widely applicable, and all of linear and non-linear types may be applied.

In other words, Equations 1 to 3 represent linear or non-linear equations as an example of equations corresponding to the boundary line discriminating a "normal" and a "patient," but may represent different equations according to a method of calculating the optimal boundary line.

$$Y = T - x_2 \quad \text{[Equation 1]}$$

(In Equation 1,
T is a boundary value between expression values of PHB2 in a normal group and a patient group,
$x_2$ is an expression value of PHB2,
when Y is a positive value, it is determined as "normal," and when Y is a negative value, it is determined as "patient.")

$$Y = 0.5857x_1 - 4.7252x_2 - 0.18652 \quad \text{[Equation 2]}$$

(In Equation 2,
$x_1$ is an expression value of PHB1,
$x_2$ is an expression value of PHB2,
when Y is a positive value, it is determined as "normal," and when Y is a negative value, it is determined as "patient.")

$$Y = 0.99 \times g(-4.536x_1 + 12.3963x_2 + 5.7187) - 9.5315 \times g(51.402x_1 - 3.3215x_2 + 49.6252) + 9.0499 \quad \text{[Equation 3]}$$

(In Equation 3,
g is a function defined by Equation 4,
when Y is a positive value, it is determined as "normal," and when Y is a negative value, it is determined as "patient.")

$$g(m) = \frac{1}{1 + e^{-m}} \quad \text{[Equation 4]}$$

In addition, the present invention provides a method of diagnosing leukemia using the leukemia diagnostic kit, which includes (1) a first step of measuring expression levels of PHB1 gene and PHB2 gene, which are obtained from leukemia specimens; and (2) a second step of diagnosing leukemia by combining the expression level of the PHB1 gene and the expression level of the PHB2 gene, which are measured in the first step.

The diagnosis of leukemia may be determined by any one equation selected from the group consisting of Equations 1 to 3 below, and the boundary values or boundary lines applied to Equations 1 to 3 in the present invention may be determined by mathematical, statistical, artificial intelligence and data-mining methods which are conventionally and widely applicable, and all of linear and non-linear types may be applied.

In other words, Equations 1 to 3 represent linear or non-linear equations as an example of equations corresponding to the boundary line discriminating a "normal" and a "patient," but may represent different equations according to a method of calculating the optimal boundary line.

$$Y = T - x_2 \quad \text{[Equation 1]}$$

(In Equation 1,
T is a boundary value between expression values of PHB2 in a normal group and a patient group,
$x_2$ is an expression value of PHB2,
when Y is a positive value, it is determined as "normal," and when Y is a negative value, it is determined as "patient.")

$$Y = 0.5857x_1 - 4.7252x_2 - 0.18652 \quad \text{[Equation 2]}$$

(In Equation 2, $x_1$ is an expression value of PHB1, $x_2$ is an expression value of PHB2, when Y is a positive value, it is determined as "normal," and when Y is a negative value, it is determined as "patient.")

$$Y=0.99 \times g(-4.536x_1+12.3963x_2+5.7187)-9.5315 \times g(51.402x_1-3.3215x_2+49.6252)+9.0499 \quad \text{[Equation 3]}$$

(In Equation 3, g is a function defined by Equation 4, when Y is a positive value, it is determined as "normal," and when Y is a negative value, it is determined as "patient.")

$$g(m) = \frac{1}{1+e^{-m}} \quad \text{[Equation 4]}$$

The leukemia in the present invention is acute myelogenous leukemia, acute lymphocytic leukemia, chronic myelogenous leukemia or chronic lymphocytic leukemia.

Hereinafter, the present invention will be described in further detail with reference to examples, but the scope and descriptions of the present invention may not be construed to be diminished or limited by the following examples. In addition, based on the disclosure of the present invention including the following examples, it is clear that the present invention in which specific experimental results are not presented can be easily carried out by those of ordinary skill in the art, and it is obvious that such alternations and modifications are also included in the accompanying claims.

Selection of Patient Group and Normal Group

Leukemia specimens used in the present invention were peripheral and bone marrow specimens obtained from 94 patients with acute myelogenous leukemia. For a normal group, peripheral blood was collected from 52 normal persons not having a specific disease through a separate basic test.

Example 1: Measurement of Gene Expression Level by PCR (1) Step 1: Collection of White Blood Cells from Peripheral and Bone Marrow Specimens Plasma was removed by centrifugation of whole blood at 3,500 rpm for 15 minutes, PBS (pH 7.4) was added to have a total volume of 5 mL, 3 ml of Lymphoprep was added thereto and then slowly mixed, and then the resulting mixture was centrifuged at 1,500 rpm for 30 min, thereby recovering a white blood cell (WBC) layer.

Sequentially, after adding PBS (pH 7.4) to have a total volume of 7 ml, the mixture was slowly mixed, and centrifuged at 1,500 rpm for 10 minutes to remove a supernatant, and then only a pellet (cells) was recovered.

(2) Step 2: RNA Extraction

In the present invention, an AMBION kit (RNAqueous phenol-free total RNA isolation_AM1912) was used.

500 µl of a lysis/binding sol. was added to a specimen and subjected to vortex mixing, followed by the addition of 500 µl of 64% ethanol (the same amount of the lysis/binging sol.). Afterward, 700 µl of the sample was put into a column, and centrifuged at 14,000 rpm for 1 minute to remove a pellet.

Subsequently, a process including adding 700 µl of Wash sol.1 to the resulting supernatant, removing a pellet by centrifugation at 14,000 rpm for 1 minute, adding 500 µl of each of Wash sol. 2 and 3 and removing a pellet by centrifugation at 14,000 rpm for 30 seconds was performed two times, and then the resulting supernatant was finally centrifuged at 14,000 rpm for 3 minutes, a column was transferred to a new tube, and then RNA was extracted by adding 40 µl of an elution buffer.

The extracted RNA was quantified using NANODROP.

(3) cDNA Synthesis

Using a commercially available Invitrogen kit (SUPERSCRIPT III First-strand synthesis system for RT-PCR 18080-051), cDNA was synthesized, and 500 ng of the total RNA quantified as described above was used in the cDNA synthesis.

(4) Conditions for Real-Time PCR 20 ng (1/25) of the synthesized cDNA (500 ng) was diluted with ultrapure water, and mixed with SYBR PCR Master Mix and PHB1 and PHB2 primers to perform real-time PCR.

Primers used to detect PHB1 and PHB2 expression are shown in Table 1 below.

TABLE 1

| Type | Sequence List | SEQ ID NO:Size | Primer | NCBI Reference Sequence |
|---|---|---|---|---|
| PHB-1 forward primer | 5'-GGA GGC GTG AAC TCT G-3' (SEQ ID NO: 1) | 1 | 175 bp | NM_002634 |
| PHB-1 reverse primer | 5'-CTG GCA CAT TAC GTG GTC GA-3' (SEQ ID NO: 2) | 2 | | |
| PHB-2 forward primer | 5'-CTT GGT TCC AGT ACC CCA TT-3' (SEQ ID NO: 3) | 3 | 115 bp | NM_001144831 |
| PHB-2 reverse primer | 5'-CGA GAC AAC ACT CGC AGG G-3' (SEQ ID NO: 4) | 4 | | |

(5) Results of Measuring Gene Expression Levels

PHB1, PHB2 and β-actin genes were subjected to a real-time quantitative PCR assay, and data was corrected by Equation 5 to overcome a difference in the degrees of gene expression between specimens (human).

As the number obtained by such a data conversion process is larger, it means that a gene expression level is relatively higher.

Figure 1A:
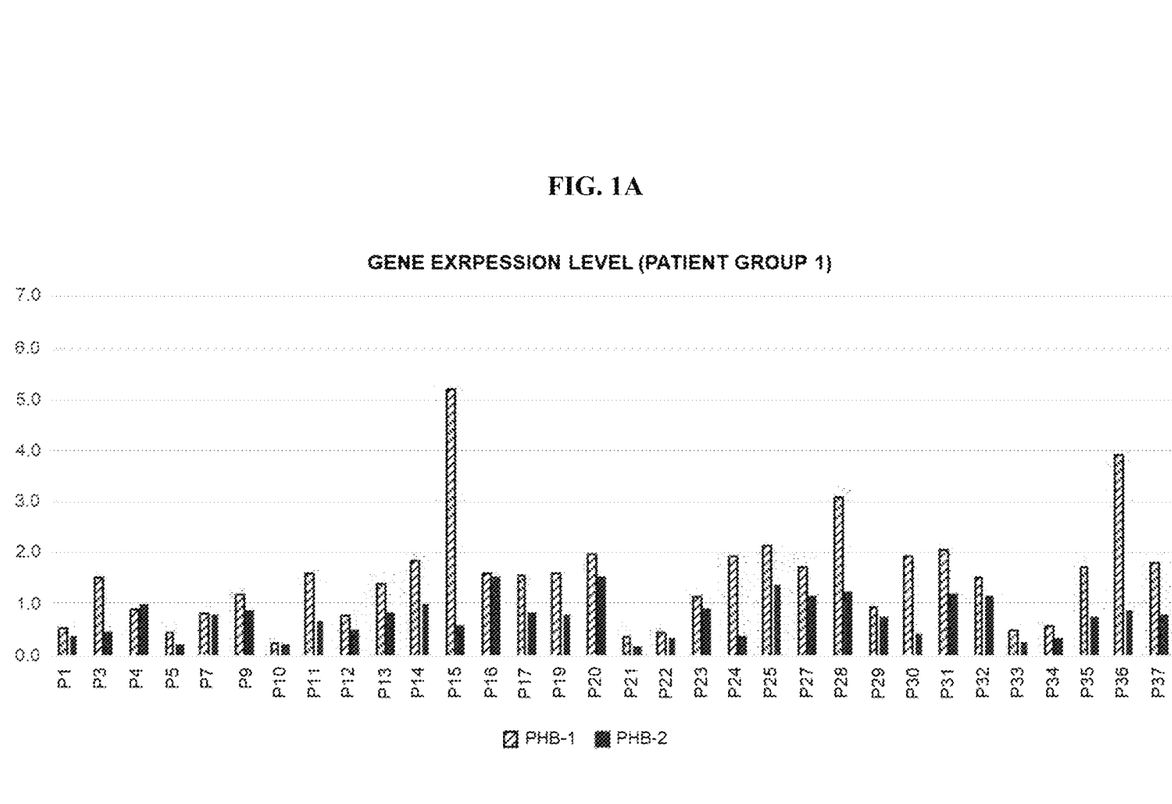
FIGS. 1A to 1C are a set of graphs illustrating mRNA PHB1 and PHB2 expression levels in specimens obtained from leukemia patient groups according to an exemplary embodiment of the present invention.
Figure 1B:
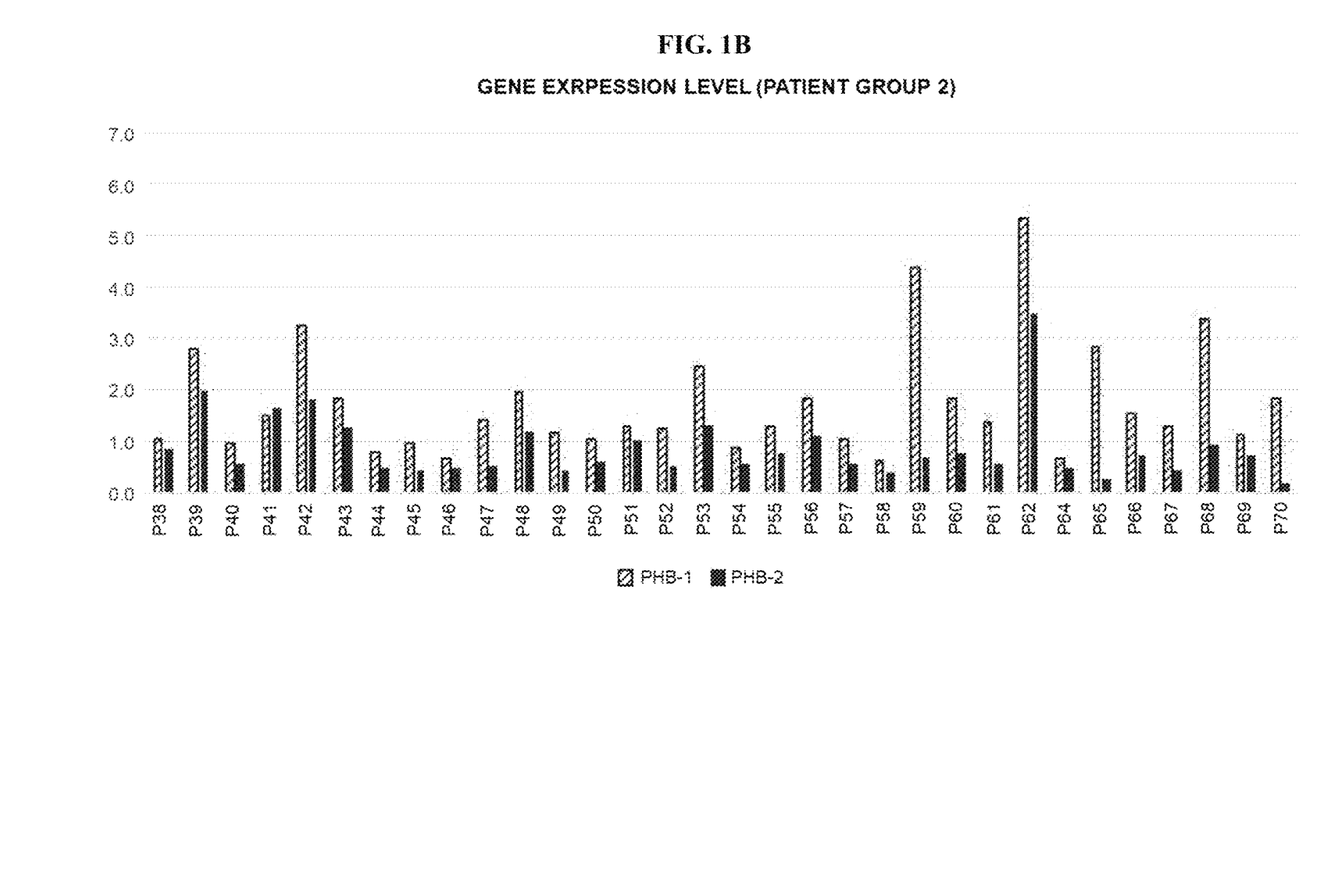
Figure 1C:
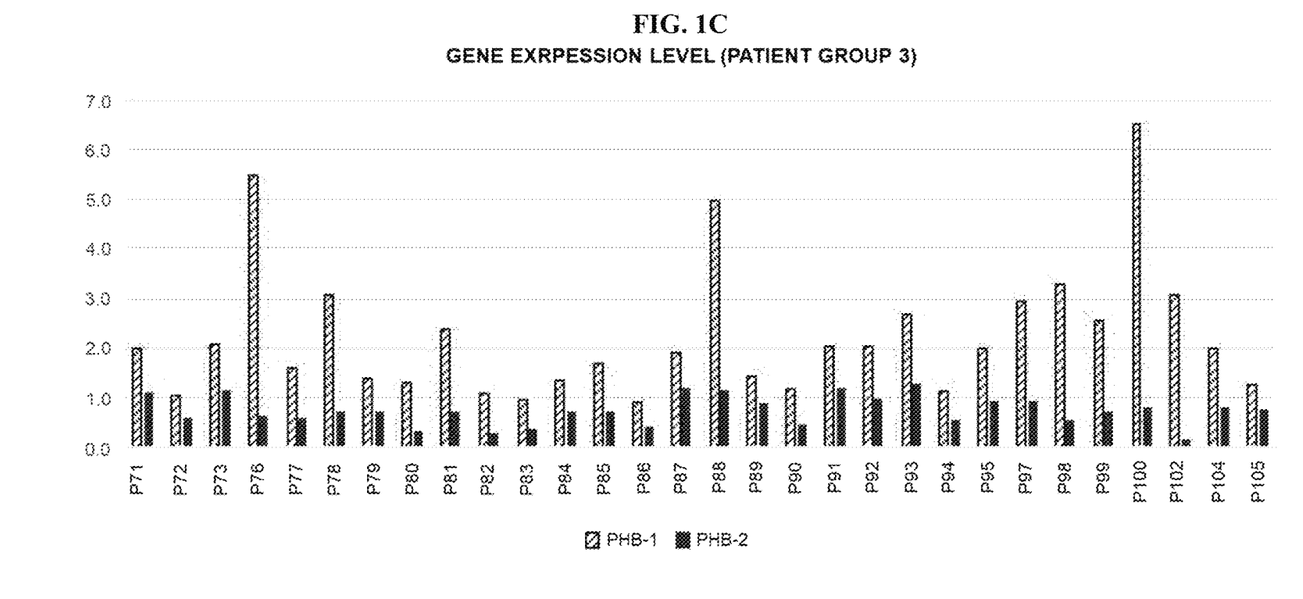
Figure 2A:
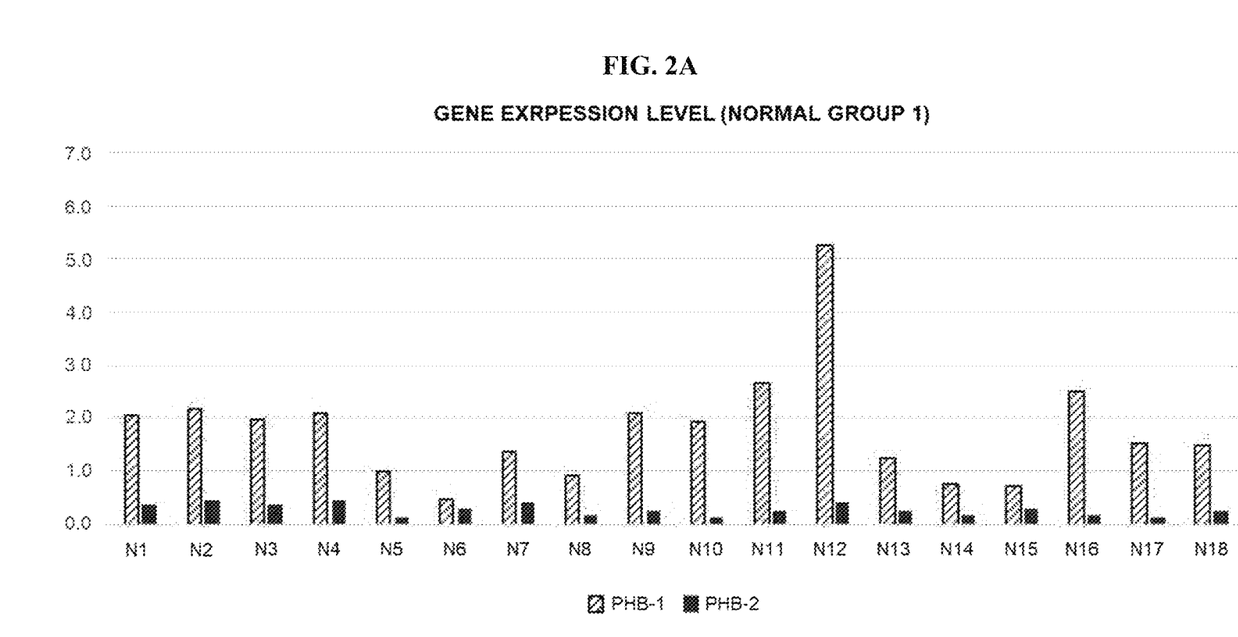
FIGS. 2A to 2C are a set of graphs illustrating PHB1 and PHB2 expression levels in specimens obtained from normal groups according to an exemplary embodiment of the present invention.
Figure 2B:
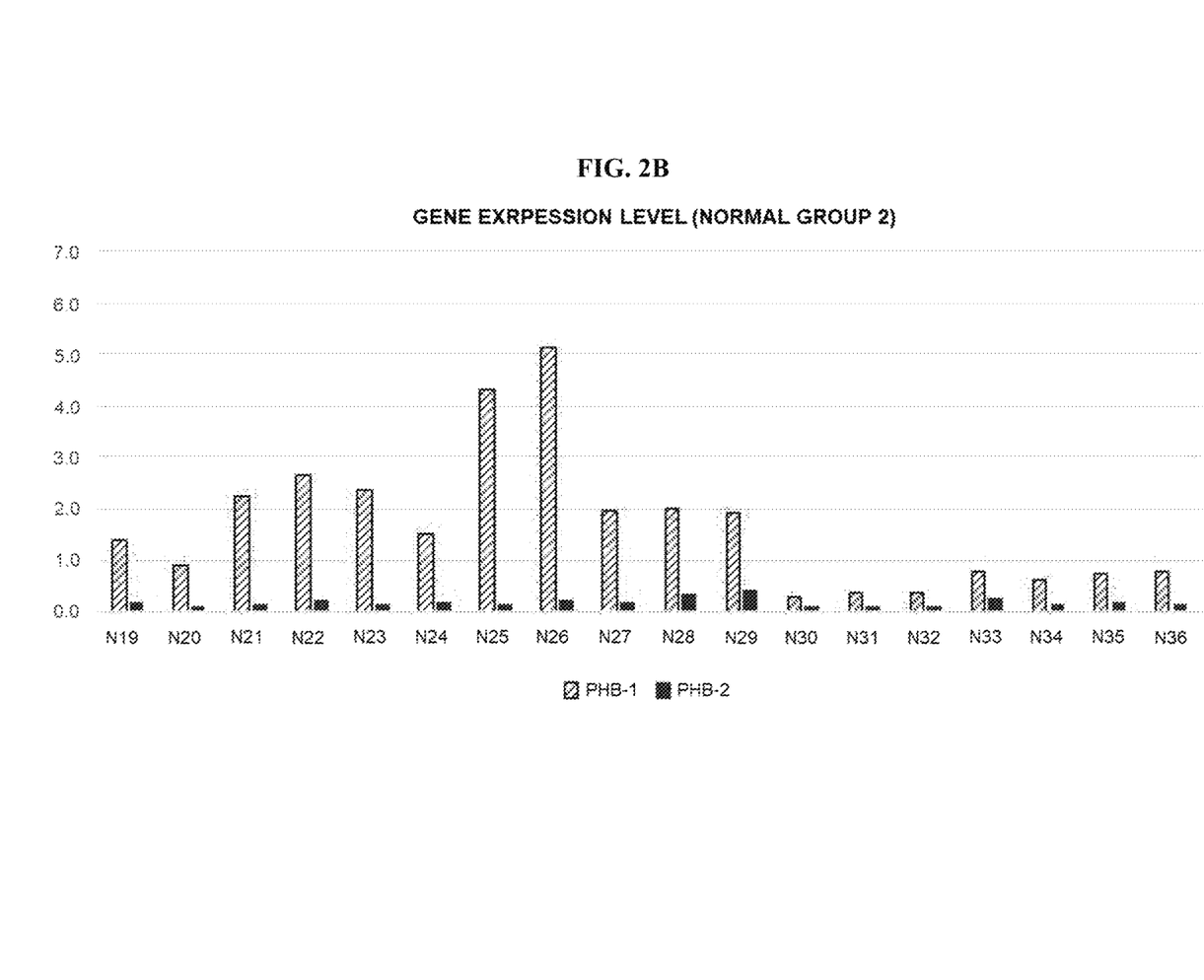
Figure 2C:
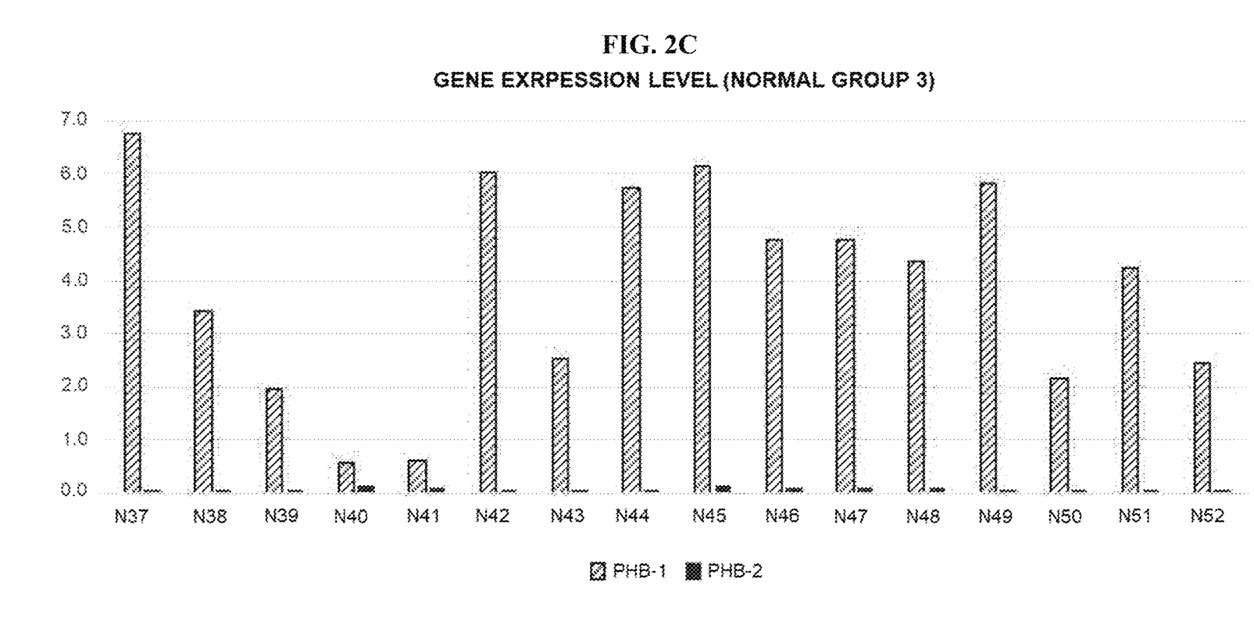

The PHB1 and PHB2 expression levels of 94 patients with leukemia are shown in Table 2 below and FIGS. 1A to 1C, and the PHB1 and PHB2 expression levels of 52 normal persons are shown in Table 3 below and FIGS. 2A to 2C.

At this time, the values measured by the real-time quantitative PCR amplification through the above-described process represent the minimum amplification cycles (Ct values) necessary for sensing the presence of a gene using a corresponding real-time quantitative PCR measurement device. In other words, the Ct values are cycles of the amplification of genes up to an amount capable of being measured using a real-time quantitative PCR device, and the higher the values, the smaller the amounts of genes originally present (expressed).

$$x_1 = 2^{-(P_1-A)}$$

$$x_2 = 2^{-(P_2-A)} \quad \text{[Equation 5]}$$

$x_1$ is an expression value of PHB1, $x_2$ is an expression value of PHB2, $P_1$ is a PCR measured value of PHB1,
$P_2$ is a PCR measured value of PHB2, and
A is a PCR measured value of actin.

TABLE 2

Expression levels of PHB1 and PHB2 in leukemia patients

| Index | PHB-1 | PHB-2 |
|---|---|---|
| P1 | 0.5154 | 0.3879 |
| P3 | 1.5303 | 0.4456 |
| P4 | 0.8790 | 1.0097 |
| P5 | 0.4245 | 0.2259 |
| P7 | 0.8201 | 0.7867 |
| P9 | 1.1760 | 0.8669 |
| P10 | 0.2167 | 0.1953 |
| P11 | 1.6176 | 0.6848 |
| P12 | 0.7867 | 0.5083 |
| P13 | 1.3985 | 0.8201 |
| P14 | 1.8453 | 0.9958 |
| P15 | 5.1832 | 0.5799 |
| P16 | 1.6176 | 1.5517 |
| P17 | 1.5734 | 0.8144 |
| P19 | 1.6064 | 0.7977 |
| P20 | 1.9641 | 1.5410 |
| P21 | 0.3721 | 0.1822 |
| P22 | 0.4395 | 0.3262 |
| P23 | 1.1598 | 0.9163 |
| P24 | 1.9237 | 0.3961 |
| P25 | 2.1493 | 1.3792 |
| P27 | 1.7098 | 1.1518 |
| P28 | 3.0820 | 1.2259 |
| P29 | 0.9163 | 0.7442 |
| P30 | 1.9370 | 0.4158 |
| P31 | 2.0617 | 1.1924 |
| P32 | 1.5198 | 1.1679 |
| P33 | 0.4678 | 0.2489 |
| P34 | 0.5759 | 0.3448 |
| P35 | 1.7098 | 0.7494 |
| P36 | 3.9010 | 0.8729 |
| P37 | 1.7948 | 0.8032 |
| P38 | 1.0453 | 0.8669 |
| P39 | 2.7970 | 2.0054 |
| P40 | 0.9618 | 0.5880 |
| P41 | 1.5093 | 1.6631 |
| P42 | 3.2577 | 1.8073 |
| P43 | 1.8453 | 1.2780 |
| P44 | 0.8032 | 0.4910 |
| P45 | 0.9685 | 0.4581 |
| P46 | 0.6661 | 0.4743 |
| P47 | 1.4378 | 0.5486 |
| P48 | 1.9641 | 1.2174 |
| P49 | 1.1598 | 0.4518 |
| P50 | 1.0525 | 0.6258 |
| P51 | 1.3230 | 1.0453 |
| P52 | 1.2780 | 0.5524 |
| P53 | 2.4518 | .3048 |
| P54 | 0.8974 | 0.5880 |
| P55 | 1.3230 | 0.7977 |
| P56 | 1.8581 | 1.1359 |
| P57 | 1.0598 | 0.5921 |
| P58 | 0.6570 | 0.3988 |
| P59 | 4.3889 | 0.6801 |
| P60 | 1.8581 | 0.7759 |
| P61 | 1.3792 | 0.5680 |
| P62 | 5.3290 | 3.4915 |
| P64 | 0.6801 | 0.4944 |
| P65 | 2.8360 | 0.2820 |
| P66 | 1.5410 | 0.7239 |
| P67 | 1.3048 | 0.4425 |
| P68 | 3.3960 | 0.9685 |
| P69 | 1.1518 | 0.7494 |
| P70 | 1.8453 | 0.2064 |
| P71 | 1.9777 | 1.1125 |
| P72 | 1.0525 | 0.5880 |
| P73 | 2.0761 | 1.1438 |
| P76 | 5.4788 | 0.6524 |
| P77 | 1.6176 | 0.5839 |
| P78 | 3.0607 | 0.7139 |
| P79 | 1.3985 | 0.7442 |

TABLE 2-continued

Expression levels of PHB1 and PHB2 in leukemia patients

| Index | PHB-1 | PHB-2 |
|---|---|---|
| P80 | 1.3048 | 0.3401 |
| P81 | 2.3848 | 0.7442 |
| P82 | 1.1049 | 0.2724 |
| P83 | 0.9753 | 0.3961 |
| P84 | 1.3415 | 0.7239 |
| P85 | 1.6863 | 0.7239 |
| P86 | 0.9099 | 0.4016 |
| P87 | 1.9104 | 1.1760 |
| P88 | 4.9721 | 1.1598 |
| P89 | 1.4279 | 0.8790 |
| P90 | 1.1679 | 0.4710 |
| P91 | 2.0333 | 1.1842 |
| P92 | 2.0475 | 0.9889 |
| P93 | 2.6645 | 1.2691 |
| P94 | 1.1438 | 0.5719 |
| P95 | 2.0054 | 0.9552 |
| P97 | 2.9564 | 0.9291 |
| P98 | 3.3032 | 0.5299 |
| P99 | 2.5559 | 0.7239 |
| P100 | 6.5154 | 0.8258 |
| P102 | 3.0607 | 0.1490 |
| P104 | 2.0054 | 0.8201 |
| P105 | 1.2780 | 0.7813 |

TABLE 3

Expression levels of PHB1 and PHB2 in normal persons

| Index | PHB-1 | PHB-2 |
|---|---|---|
| N1 | 2.0475 | 0.3696 |
| N2 | 2.1944 | 0.4518 |
| N3 | 1.9641 | 0.3852 |
| N4 | 2.0905 | 0.4613 |
| N5 | 1.0167 | 0.1400 |
| N6 | 0.4613 | 0.3044 |
| N7 | 1.3697 | 0.4275 |
| N8 | 0.9355 | 0.1609 |
| N9 | 2.1051 | 0.2455 |
| N10 | 1.9237 | 0.1430 |
| N11 | 2.6645 | 0.2323 |
| N12 | 5.2556 | 0.4100 |
| N13 | 1.2430 | 0.2650 |
| N14 | 0.7494 | 0.1797 |
| N15 | 0.7289 | 0.2801 |
| N16 | 2.4861 | 0.1712 |
| N17 | 1.5198 | 0.1106 |
| N18 | 1.4680 | 0.2388 |
| N19 | 1.3985 | 0.1861 |
| N20 | 0.9163 | 0.1202 |
| N21 | 2.2561 | 0.1654 |
| N22 | 2.6461 | 0.2405 |
| N23 | 2.3519 | 0.1631 |
| N24 | 1.5093 | 0.1861 |
| N25 | 4.3285 | 0.1362 |
| N26 | 5.1474 | 0.2152 |
| N27 | 1.9777 | 0.1848 |
| N28 | 2.0054 | 0.3521 |
| N29 | 1.9370 | 0.4245 |
| N30 | 0.3086 | 0.0970 |
| N31 | 0.3773 | 0.1228 |
| N32 | 0.3570 | 0.1253 |
| N33 | 0.7652 | 0.2650 |
| N34 | 0.6258 | 0.1522 |
| N35 | 0.7340 | 0.1953 |
| N36 | 0.7652 | 0.1620 |
| N37 | 6.7452 | 0.0301 |
| N38 | 3.4197 | 0.0475 |
| N39 | 1.9641 | 0.0334 |
| N40 | 0.5680 | 0.1532 |
| N41 | 0.6258 | 0.1011 |
| N42 | 5.9954 | 0.0044 |
| N43 | 2.5208 | 0.0188 |

TABLE 3-continued

Expression levels of PHB1 and PHB2 in normal persons

| Index | PHB-1 | PHB-2 |
|---|---|---|
| N44 | 5.7114 | 0.0185 |
| N45 | 6.1214 | 0.1501 |
| N46 | 4.7696 | 0.1099 |
| N47 | 4.7696 | 0.1069 |
| N48 | 4.3586 | 0.1069 |
| N49 | 5.7912 | 0.0265 |
| N50 | 2.1344 | 0.0041 |
| N51 | 4.2101 | 0.0331 |
| N52 | 2.4181 | 0.0397 |

As shown in Tables 2 and 3, according to the present invention, a patient and a normal person can be distinguished only with the PHB2 values. More specifically, as confirmed in FIGS. 1A to 1C and FIGS. 2A to 2C, it can be observed that "PHB1" does not show a significant difference between patients and normal persons, and "PHB2" is more highly expressed in the patient group than in the normal group.

Therefore, based on the boundary value of PHB2, when a value is higher than the boundary value, it was diagnosed as "patient," and when a value is lower than the boundary value, it was diagnosed as "normal".

Example 2: Analysis of Measured Values and Diagnosis (1) Diagnosis of Leukemia Using PHB2 Expression Level To significantly distinguish "patient" and "normal" according to PHB1 and PHB2 expression levels shown in Tables 2 and 3, measured values were analyzed by Equation 4 below.

Figure 3A:
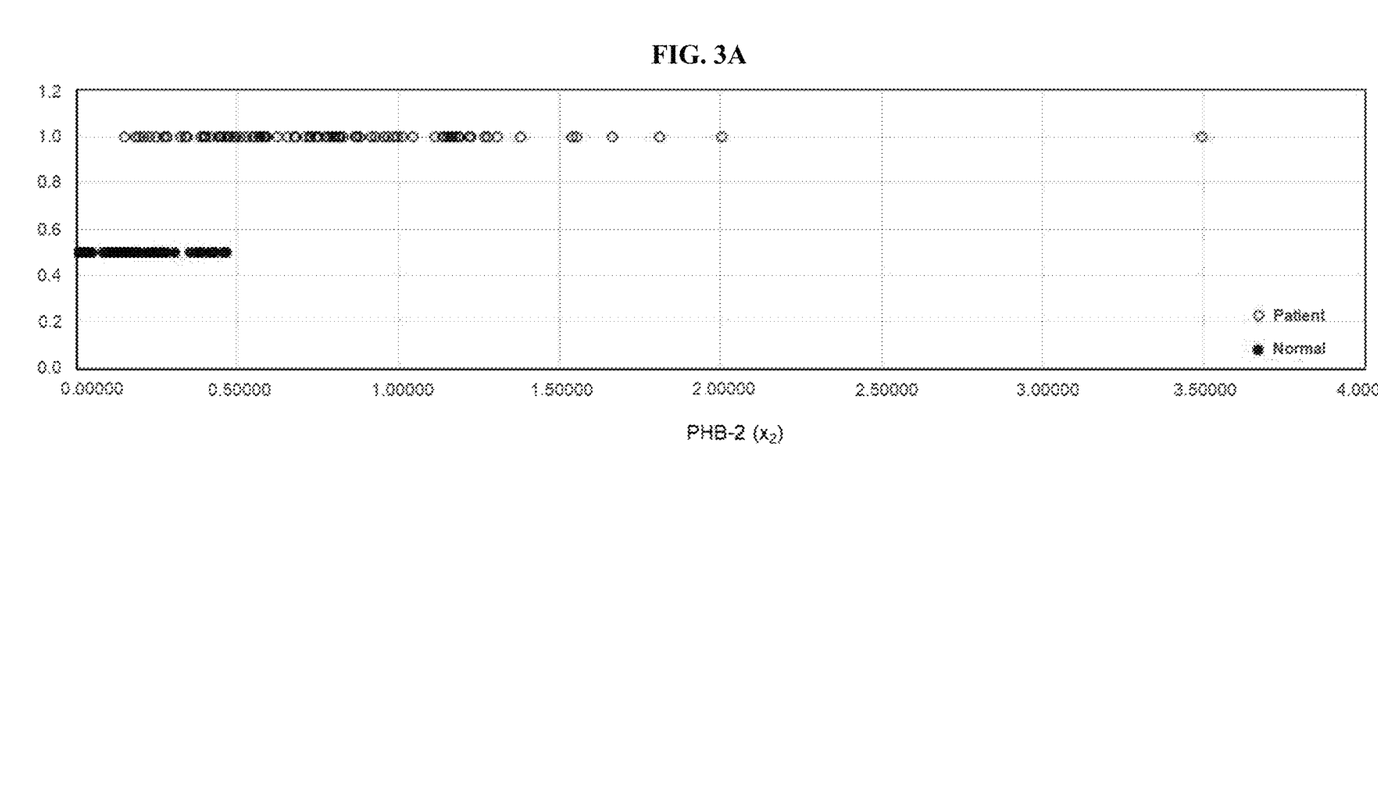
FIGS. 3A to 3B are a set of graphs an expression level of PHB2 in specimens obtained from a leukemia patient group and a normal group according to an exemplary embodiment of the present invention.
Figure 3B:
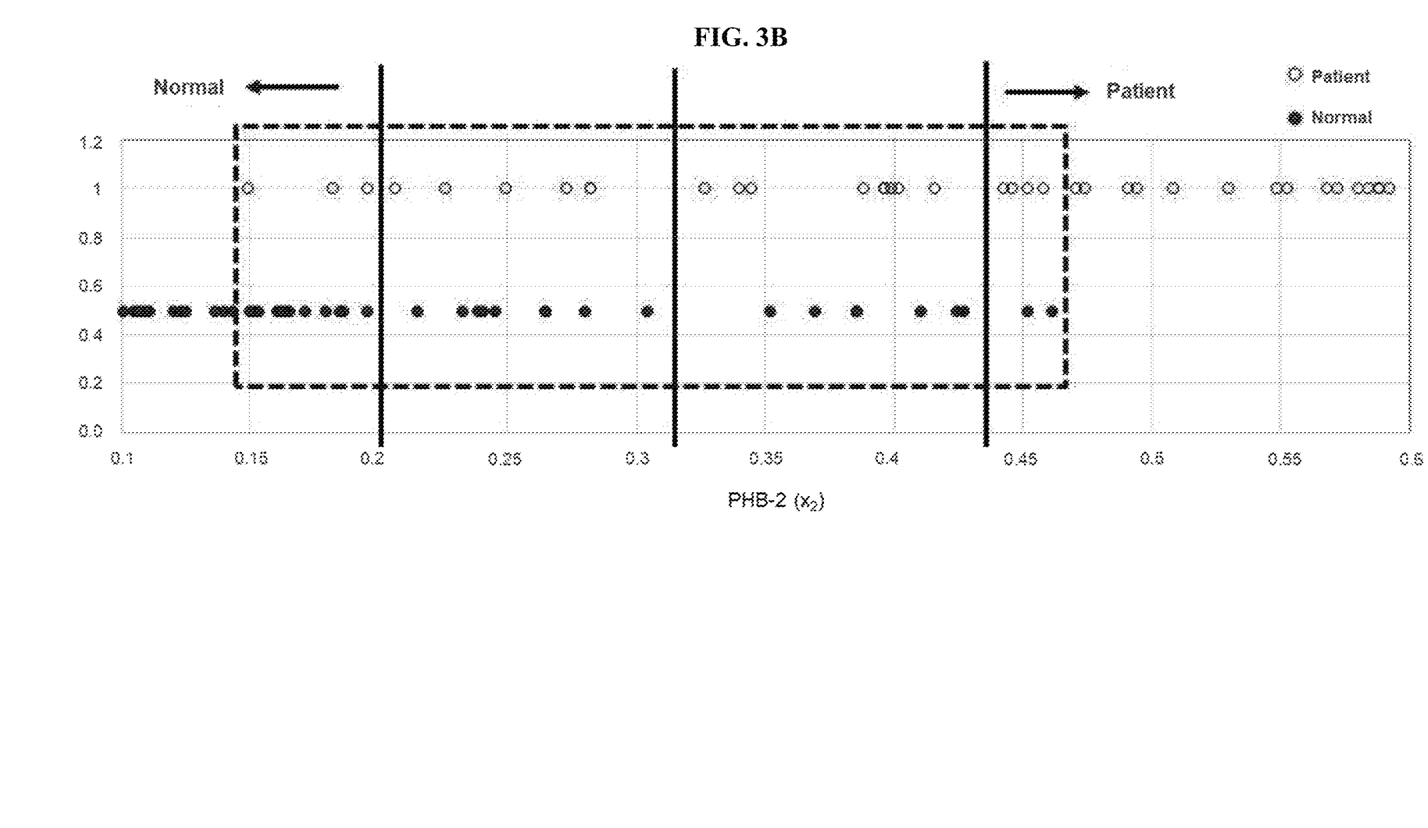

FIG. 3A shows only the PHB2 expression levels confirmed in Tables 2 and 3, and then, to eliminate difficulty in observation caused by overlapping generated when single values are present on one axis, for convenience, the patient group is represented on the line of 1.0 of the vertical axis, and the normal group is represented on the line of 0.5 of the vertical axis, and as a result of enlarging only the region in which PHB2 values of the normal group and the patient group overlap in FIG. 3B, it was confirmed that the region represented by the dotted line is the overlapping section (0.14~0.47).

In the overlapping region, three vertical lines (0.2, 0.315, 0.435) in FIG. 3B represent the examples of boundary values, and when the middle vertical line (0.315) is selected as the boundary line between the normal and the patient, among the specimens in Tables 2 and 3, 8 patients are diagnosed as "normal," and 8 patients are diagnosed as "patient." Such a diagnostic method may be defined by Equation 1 below.

$$Y=T-x_2 \qquad \text{[Equation 1]}$$

(In Equation 1,

T is a boundary value between expression values of PHB2 in a normal group and a patient group, $x_2$ is an expression value of PHB2, when Y is a positive value, it is determined as "normal," and when Y is a negative value, it is determined as "patient.")

In other words, when T=0.315 is applied to the diagnostic method according to Equation 1, diagnostic results for the specimens in Tables 2 and 3 may have the diagnosis accuracy as shown in Table 4 below.

TABLE 4

| Diagnostic group | Patient | Normal | Total |
|---|---|---|---|
| Patient | 86 (91.5%) | 8 (8.5%) | 94 (100%) |
| Normal | 8 (15.4%) | 44 (84.6%) | 52 (100%) |

(2) Leukemia Diagnosis Using PHB1 and PHB2 Expression Levels-1

Figure 4:
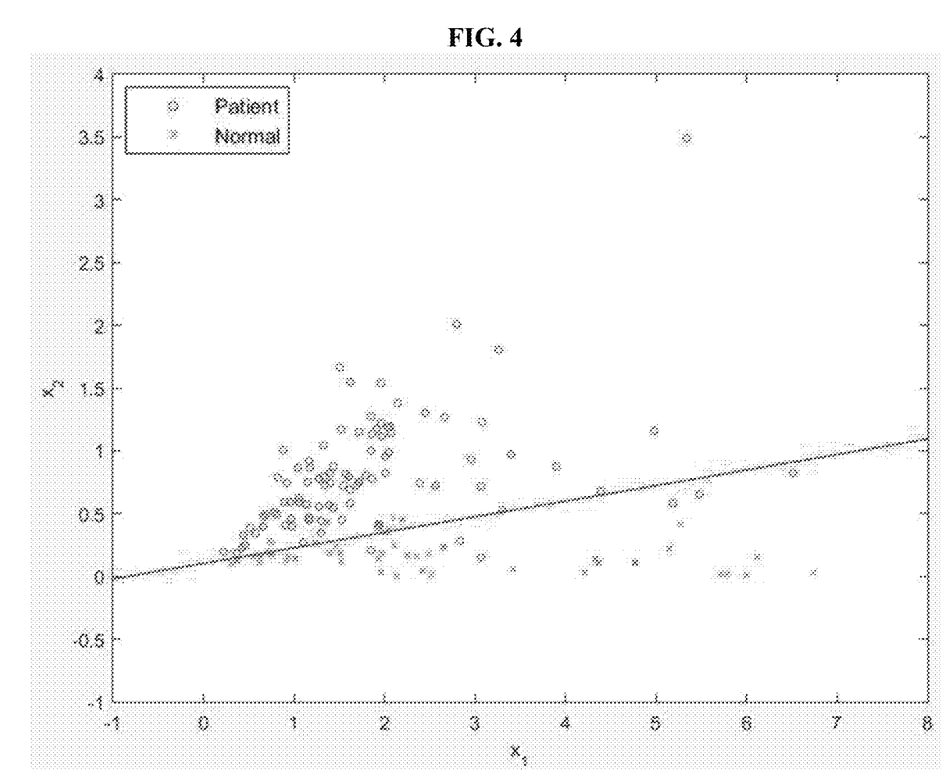
FIG. 4 is a graph illustrating that a linear boundary line for diagnosing leukemia is shown in coordinates on a two-dimensional plane with a horizontal axis indicating PHB1 and a vertical axis indicating PHB2 according to an exemplary embodiment of the present invention.

In addition, in the present invention, provided that the horizontal axis presents PHB1, the vertical axis presents PHB2, and corresponding values are represented as coordinates on the two-dimensional plane, according to the diagnostic method by combining the PHB1 and PHB2 expression levels in Tables 2 and 3, as shown in FIG. 4, when the values are located above the boundary line that distinguishes the patient group and the normal group, they are diagnosed as "patient," and when the values are located below the boundary line that distinguishes the patient group and the normal group, they are diagnosed as "normal," which can be represented by Equation 2 below.

$$Y=0.5857x_1-4.7252x_2-0.18652 \qquad \text{[Equation 2]}$$

(In Equation 2, $x_1$ is an expression value of PHB1, $x_2$ is an expression value of PHB2, when Y is a positive value, it is determined as "normal," and when Y is a negative value, it is determined as "patient.").

According to the diagnostic method by Equation 2, as the result of diagnosing the specimens in Tables 2 and 3, diagnosis accuracy shown in Table 5 below may be obtained.

TABLE 5

| Diagnostic group | Patient | Normal | Total |
|---|---|---|---|
| Patient | 88 (93.6%) | 6 (6.4%) | 94 (100%) |
| Normal | 12 (23.1%) | 40 (76.9%) | 52 (100%) |

(3) Leukemia Diagnosis Using PHB1 and PHB2 Expression Levels-2

In addition, the present invention was applied to the diagnostic method using a non-linear boundary line by combining the PHB1 and PHB2 expression levels in Tables 2 and 3.

Figure 5:
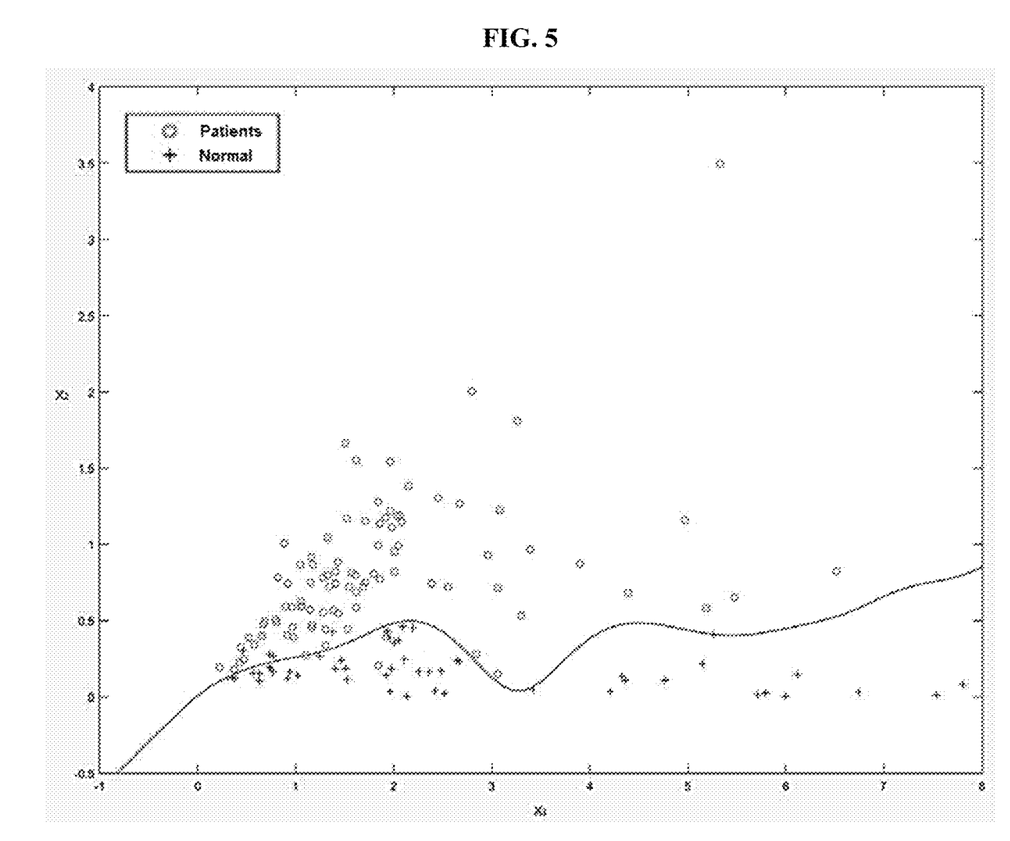
FIG. 5 is a graph illustrating that a non-linear boundary line for diagnosing leukemia is shown in coordinates on a two-dimensional plane with a horizontal axis indicating PHB1 and a vertical axis indicating PHB2 according to an exemplary embodiment of the present invention.

When the non-linear boundary line shown in FIG. 5 is applied, diagnosis accuracy with respect to the specimens in Tables 2 and 3, shown in Table 6, may be obtained by Equations 3 and 4.

$$Y=0.99 \times g(-4.536x_1+12.3963x_2+5.7187)-9.5315 \times g(51.402x_1-3.3215x_2+49.6252)+9.0499 \qquad \text{[Equation 3]}$$

(In Equation 3, g is a function defined by Equation 4, when Y is a positive value, it is determined as "normal," and when Y is a negative value, it is determined as "patient.")

$$g(m) = \frac{1}{1+e^{-m}} \qquad \text{[Equation 4]}$$

TABLE 6

| Diagnostic group | Patient | Normal | Total |
|---|---|---|---|
| Patient | 90 (95.7%) | 4 (4.3%) | 94 (100%) |
| Normal | 4 (7.7%) | 48 (92.3%) | 52 (100%) |

The invention claimed is:

1. A method of diagnosing leukemia in a subject, the method comprising:

obtaining mRNA of a prohibitin-1 (PHB1) gene and mRNA of a prohibitin-2 (PHB2) gene from the subject;

synthesizing cDNAs by using the mRNAs of the PHB1 gene and the mRNA of the PHB2 gene as a template;

amplifying the cDNAs;

measuring the amplified cDNAs to obtain expression value of the prohibitin-1 (PHB1) gene and expression value of the prohibitin-2 (PHB2) gene;

diagnosing leukemia, by using any one equation selected from the group consisting of Equations 2 and 3:

$$Y = 0.5857 x_1 - 4.7252 x_2 - 0.18652 \quad \text{[Equation 2]}$$

in Equation 2, $x_1$ is the expression value of PHB1, $x_2$ is the expression value of PHB2, when Y is a positive value, it is determined as "normal," and when Y is a negative value, it is determined as "patient"; and $$Y = 0.99 \times g(-4.536 x_1 + 12.3963 x_2 + 5.7187) - 9.5315 \times g(51.402 x_1 - 3.3215 x_2 + 49.6252) + 9.0499 \quad \text{[Equation 3]}$$

in Equation 3, g is a function defined by Equation 4, when Y is a positive value, it is determined as "normal," and when Y is a negative value, it is determined as "patient":

$$g(m) = \frac{1}{1+e^{-m}}, \quad \text{[Equation 4]}$$

wherein the amplifying of the cDNAs comprises using a forward primer of SEQ ID NO: 1 and a reverse primer of SEQ ID NO: 2 to amplify the cDNA of the PHB1 gene, and a forward primer of SEQ ID NO: 3 and a reverse primer of SEQ ID NO: 4 to amplify the cDNA of the PHB2 gene.

2. The method according to claim 1, wherein the amplifying of the cDNAs comprises performing RT-PCR with respect to the mRNA of the PHB1 gene and the mRNA of the PHB2 gene.

3. The method according to claim 1, wherein the obtaining of the mRNAs comprises:
collecting white blood cells from peripheral or bone marrow specimens of the subject; and
extracting mRNA from the collected white blood cells.

4. The method of claim 1, wherein the leukemia is acute myelogenous leukemia, acute lymphocytic leukemia, chronic myelogenous leukemia or chronic lymphocytic leukemia.

\* \* \* \* \*